United States Patent [19]

Tanaka et al.

[11] Patent Number: 4,617,155

[45] Date of Patent: Oct. 14, 1986

[54] NOVEL LYSINE SALT CRYSTALS AND PROCESS FOR PRODUCTION THEREOF

[75] Inventors: Kiyoshi Tanaka, Tokyo; Yoshihiro Koga, Saga; Masaru Saeki, Fujisawa; Tetsuya Kaneko, Kawasaki; Tetsuya Kawakita, Yokohama, all of Japan

[73] Assignee: Ajinomoto Co., Inc., Tokyo, Japan

[21] Appl. No.: 701,372

[22] Filed: Feb. 12, 1985

[30] Foreign Application Priority Data

Feb. 13, 1984 [JP] Japan .................................. 59-24876

[51] Int. Cl.[4] .................. C07C 53/126; C07C 101/24; A23J 1/00
[52] U.S. Cl. ................................ 260/501.12; 426/656
[58] Field of Search .................................... 260/501.12

[56] References Cited

U.S. PATENT DOCUMENTS

| 2,536,360 | 1/1951 | Emmick et al. | 260/501.11 |
| 2,934,561 | 4/1960 | Rogers | 260/501.12 |
| 3,845,110 | 10/1974 | Fahnenstich et al. | 260/501.12 |

FOREIGN PATENT DOCUMENTS 2257925 11/1972 Fed. Rep. of Germany ... 260/501.1

*Primary Examiner*—J. E. Evans
*Attorney, Agent, or Firm*—Oblon, Fisher, Spivak, McClelland & Maier

[57] ABSTRACT

An equimolar salt of lysine and 2-hydroxy-4-methylthiobutyric acid is disclosed along with a process of preparing this salt.

3 Claims, No Drawings

NOVEL LYSINE SALT CRYSTALS AND PROCESS FOR PRODUCTION THEREOF

BACKGROUND OF THE INVENTION

1. Field of the Invention

This invention relates to lysine salt crystals and to processes for the production thereof.

2. Description of the Prior Art

Lysine is well known to be an essential amino acid and must be provided in the diet of many animals, including most mammals. Lysine is typically provided as an animal feed additive in the form of lysine hydrochloride. However, lysine hydrochloride absorbs moisture and at times undergoes aggregation. Thus, lysine hydrochloride proves undesirable from the standpoint of convenience of use and commercial value, and a substitute therefore is needed.

2-Hydroxy-4-methylthiobutyric acid, otherwise called methionine hydroxy analog, is a compound having a hydroxyl group in the place of the amino group of methionine. It is a known intermediate in the biosynthesis of methionine. Since it is easily converted into methionine within an animal body, it is also utilized as an animal feed in the place of methionine. This compound, however, cannot be easily produced in the form of crystals. Generally, therefore, it is marketed in the form of a concentrated aqueous solution. This concentrated aqueous solution poses a problem in terms of handling since it has a strong acidity, being even below pH 1.0 when highly concentrated. Thus, a substitute for 2-hydroxy-4-methylthiobutyric acid is likewise needed.

SUMMARY OF THE INVENTION

Accordingly, it is an object of this invention to provide a new salt form of lysine useful as an animal feed additive.

It is likewise an object of this invention to provide an additive capable of supplying 2-hydroxy-4-methylthiobutyric acid.

These and other objects of the invention have been accomplished by providing a crystalline salt material consisting of equimolar amounts of lysine and 2-hydroxy-4-methylthiobutyric acid. A process for producing such salts, which have decided advantages over prior salts of lysine with regard to moisture absorption and aggregation, is also provided.

DESCRIPTION OF THE PREFERRED EMBODIMENTS

The present invention arose as the result of studies directed toward overcoming the disadvantageous properties of known salts of lysine. As a result of these studies, the inventors discovered that an equimolar salt crystal of lysine and 2-hydroxy-4-methylthiobutyric acid would absorb moisture only minimally and only aggregate sparingly. These studies led to the perfection of the present invention.

Specifically, this invention provides an equimolar salt crystal of lysine and 2-hydroxy-4-methylthiobutyric acid and a process for the production thereof.

The novel lysine-2-hydroxy-4-methylthiobutryic acid salt crystals provided by this invention are less hydroscopic than lysine hydrochloride and easier to handle than 2-hydroxy-4-methylthiobutyric acid (later referred to herein as "MHA"). It is highly useful as an animal feed additive, since it acts as a source for both methionine and lysine.

The production of lysine-2-hydroxy-4-methylthiobutyric acid equimolar salt crystals is effected by causing lysine and 2-hydroxy-4-methylthiobutyric acid to react with each other in an aqueous medium and subsequently concentrating, crystallizing, and separating the resulting reaction mixture. The two starting materials are well-known organic chemicals and can be obtained from commercial sources or by synthesis using published techniques.

Lysine may be in either of the two forms, the L-form or the DL-form. It can be advantageously used in an amount equimolar to or slightly in excess relative to the amount of 2-hydroxy-4-methylthiobutyric acid. The equimolar salt is obtained even when 2-hydroxy-4-methylthiobutyric acid is used in an amount twice the molar equivalence of lysine. Preferred molar ratios of lysine to MHA used in the production of the salt are in the range from 1.1:1 to 1:2 with approximately equimolar ratios being preferred.

Production of lysine-MHA equimolar salt crystals can be effected either by preparing an aqueous solution of lysine and adding MHA, either as a solid or dissolved in a aqueous liquid, to the original solution or by carrying out the reaction in the reverse order (i.e., adding lysine to a solution of MHA). A preferred aqueous medium is water, with solutions of water and lower alcohols (especially those with 1-4 carbons) being secondarily preferred. Other low-molecular-weight organic solvents miscible with water, such as acetone, may also be used. Organic solvents are preferably present in no more than 20, more preferably no more than 10, percent by weight.

The starting materials may be dissolved in the aqueous solution either at room temperature or at an elevated temperature below the boiling point of the aqueous solution. Preferred are temperatures of no more than 70° C., preferably no more than 60° C. The starting compounds may be dissolved at any concentration up to the saturation limits. Higher concentrations are preferred in order to minimize the amount of concentrating that must be carried out during later steps of collecting the crystals.

Once the starting materials have been added together in an aqueous medium, the resulting solution is concentrated in order to allow removal of the salt, optionally with heating. If the solution is heated, it is preferred that a temperature of no more than 70° C., preferably no more than 60° C., be used. Reduced pressure may be used if desired. The process of obtaining salts by concentrating solutions in which the salts are prepared is a standard laboratory procedure, and many modifications are known that can readily be adapted to the process of the present invention.

If desired, crude crystals obtained by the initial concentration and separation steps (e.g., separation may be effected by decantation or filtration) can optionally be treated with activated charcoal or other means of removing dissolved impurities, such as absorbing impurities on a column containing a absorbing resin.

The invention now being generally described, the same will be better understood by reference to certain specific examples which are included here for illustration only and are not to be considered limiting of the invention unless otherwise stated.

EXAMPLE 1

To 100 g of 2-hydroxy-4-methylthiobutyric acid (aqueous 88% MHA solution produced by Monsanto Company and marketed under trademark designation of "ALIMET"), 67.8 g of L-lysine was added. These amounts correspond to a MHA:L-lysine molar ratio of 1.3:1. The resulting solution was concentrated to 1.5 times the original level and then cooled from 60° C. to 20° C. and subjected to crystallization and separation to obtain 64 g of crude crystals. The crude crystals were dissolved in 300 ml of water. The resulting solution and 4 g of activated carbon added thereto were stirred at 60° C. for one hour and then filtered. The filtrate was concentrated to 10 times the original level, cooled from 60° C. to 20° C., and subjected to crystallization to afford 6.0 g of 1:1 mole ratio salt of L-lysine-2-hydroxy-4-methylthiobutyric acid.

The physical properties of the product were as follows.

| (1) Elementary analysis: | | Calculated | Found |
|---|---|---|---|
| For $C_{11}H_{24}O_5N_2S$ | C | 44.57% | 44.44% |
| | H | 8.18 | 8.33 |
| | N | 9.45 | 9.54 |
| | O | 26.99 | 26.98 |
| | S | 10.82 | 10.70 |
| (2) Molecular weight: | 296.43 (identified to be $C_{11}H_{24}O_5N_2S$ by elementary analysis) | | |
| (3) Melting point: | 169.5° C. | | |
| (4) Solubility in solvents: | Readily soluble in water and sparingly soluble in methanol and ethanol. | | |
| (5) Crystal Form: | Needles | | |

EXAMPLE 2

By repeating the procedure of Example 1 using 170 g of "ALIMET" and 146 g of L-lysine (molar ratio MHA:L-lysine=1:1), 53 g of crude crystals were obtained. By refining the crude crystals by the procedure of Example 1, there were obtained 4.3 g of 1:1 mole ratio salt crystals of L-lysine-2-hydroxy-4-methylthiobutyric acid.

EXAMPLE 3

By repeating the procedure of Example 1 using 170 g of "ALIMET" and 73 g of L=lysine (molar ratio MHA:L-lysine=2:1), 23 g of crude crystals were obtained. By refining the crude crystals by the procedure of Example 1, there were obtained 3.0 g of 1:1 mole ratio salt crystals of L-lysine-2-hydroxy-4-methylthiobutyric acid.

COMPARATIVE EXPERIMENT

In dessicators kept under a relative humidity (RH) of 54%, 3.0 g of 1:1 mole ratio salt crystals of L-lysine-2-hydroxy-4-methylthiobutyric acid and 3.0 g of L-lysine hydrochloride were separately left standing at rest for 20 days. At the end of this period, they were tested for moisture gain. The same test was repeated under a relative humidity of 66%. The results are shown below.

The two samples used had initial water content of 0.2%.

| | RH 54% | RH 66% |
|---|---|---|
| Lysine hydrochloride | 3.0% | 7.5% |
| Lysine 2-hydroxy-4-methylthiobutyric acid salt | 1.8% | 1.8% |

It is noted from the foregoing table that the novel lysine salt of this invention has extremely low hydroscopicity as compared with lysine hydrochloride, and that, once an initial low water content was achieved, no increase in water content occured with an increase in relative humidity.

The invention now being fully described, it will be apparent to one of ordinary skill in the art that many variations and modifications thereof can be made without departing from the spirit or scope of the invention as set forth herein.

What is new and desired to be secured by Letters Patent of the United States is:

1. An equimolar salt of lysine and 2-hydroxy-4-methylthiobutyric acid.
2. The salt of claim 1, wherein said salt is in crystalline form.
3. The salt of claim 2, wherein said salt contains no more than 1.8% moisture.

* * * * *